United States Patent [19]

Smith

[11] Patent Number: 5,320,635
[45] Date of Patent: Jun. 14, 1994

[54] SURGICAL DEVICE WITH SURGICAL ELEMENT REMOVABLY CONNECTED TO DRIVE ELEMENT

[75] Inventor: Graham Smith, Plaistow, N.H.

[73] Assignee: Smith & Nephew Dyonics, Inc., Andover, Mass.

[21] Appl. No.: 978,178

[22] Filed: Nov. 17, 1992

Related U.S. Application Data

[63] Continuation of Ser. No. 600,531, Oct. 19, 1990, abandoned.

[51] Int. Cl.⁵ ............................................. A61B 17/32
[52] U.S. Cl. ..................................... 606/180; 606/167; 606/170; 408/713; 604/22
[58] Field of Search .................... 604/23, 25; 606/79, 606/80, 167, 169, 170, 180, 171, 166, 163, 173; 128/751, 752; 408/1, 713, 125; 30/205, 206, 216, 240, 347; 433/131, 132

[56] References Cited

U.S. PATENT DOCUMENTS

| | | |
|---|---|---|
| 745,722 | 12/1903 | Freeman . |
| 3,618,611 | 11/1971 | Urban ........................ 606/170 |
| 3,734,099 | 5/1973 | Bender et al. . |
| 3,837,345 | 9/1974 | Matar ........................ 606/167 |
| 3,847,154 | 11/1974 | Nordin . |
| 3,937,222 | 2/1976 | Banko . |
| 3,945,375 | 3/1976 | Banko . |
| 4,020,847 | 5/1977 | Clark, III . |
| 4,071,029 | 1/1978 | Richmond et al. ............ 606/180 |
| 4,167,943 | 9/1979 | Banko . |
| 4,167,944 | 9/1979 | Banko . |
| 4,200,106 | 4/1980 | Douvas et al. ............... 606/170 |
| 4,203,444 | 5/1980 | Bonnell et al. . |
| 4,246,902 | 1/1981 | Martinez . |
| 4,265,231 | 5/1981 | Scheller, Jr. et al. . |
| 4,274,414 | 6/1981 | Johnson et al. . |
| 4,320,762 | 3/1982 | Haddad . |
| 4,436,091 | 3/1984 | Banko . |
| 4,445,509 | 5/1984 | Auth . |
| 4,466,429 | 8/1984 | Loscher et al. . |
| 4,497,320 | 2/1985 | Nicholson et al. . |
| 4,512,344 | 4/1985 | Barber . |
| 4,517,977 | 5/1985 | Frost . |
| 4,522,206 | 6/1985 | Whipple et al. . |
| 4,541,423 | 9/1985 | Barber . |
| 4,589,412 | 5/1986 | Kensey . |
| 4,589,414 | 5/1986 | Yoshida et al. ............... 606/79 |
| 4,598,710 | 7/1986 | Kleinberg et al. ............ 606/170 |
| 4,603,694 | 8/1986 | Wheeler . |
| 4,631,052 | 12/1986 | Kenney . |
| 4,646,738 | 3/1987 | Trott ........................ 128/752 |
| 4,662,371 | 5/1987 | Whipple et al. . |
| 4,672,965 | 6/1987 | Baum . |
| 4,681,106 | 7/1987 | Kenney et al. . |
| 4,690,140 | 9/1987 | Mecca . |
| 4,696,667 | 9/1987 | Masch . |
| 4,705,038 | 11/1987 | Sjostrom et al. . |
| 4,706,659 | 11/1987 | Matthews et al. ............ 606/80 |
| 4,723,545 | 2/1988 | Nixon et al. . |

(List continued on next page.)

FOREIGN PATENT DOCUMENTS

| | | |
|---|---|---|
| 3828478A1 | 5/1989 | Fed. Rep. of Germany . |
| 3829478A1 | 5/1989 | Fed. Rep. of Germany . |
| 3906301A | 12/1989 | Fed. Rep. of Germany . |

(List continued on next page.)

OTHER PUBLICATIONS

J. C. Palmaz, "Atherosclerotic Rabbit Aortas: Expandable Intraluminal Grafting¹", Department of Radiology, 1986.

Primary Examiner—Stephen C. Pellegrino
Assistant Examiner—Glenn Dawson
Attorney, Agent, or Firm—Fish & Richardson

[57] ABSTRACT

A surgical device having a surgical element removably connected to a drive element so that drive torque is transmitted to the surgical element as the drive element rotates, while allowing the surgical element at least one degree of freedom of motion relative to the drive element; a retaining element maintains the drive and surgical elements in torque-transmitting relation during operation of the device.

34 Claims, 4 Drawing Sheets

U.S. PATENT DOCUMENTS

| | | |
|---|---|---|
| 4,738,256 | 4/1988 | Freeman et al. . |
| 4,739,762 | 4/1988 | Palmaz . |
| 4,756,309 | 7/1988 | Sachse et al. . |
| 4,770,174 | 9/1988 | Luckman et al. . |
| 4,790,312 | 12/1988 | Capuano, Sr. et al. . |
| 4,834,729 | 5/1989 | Sjostrom . |
| 4,842,578 | 6/1989 | Johnson et al. . |
| 4,844,064 | 7/1989 | Thimsen et al. . |
| 4,850,354 | 7/1989 | McGurk-Burleson . |
| 4,867,155 | 9/1989 | Isaacson . |
| 4,923,441 | 5/1990 | Shuler . |
| 4,983,179 | 1/1991 | Sjostrom ............... 606/170 |
| 5,047,008 | 9/1991 | Juan et al. ............. 604/22 |
| 5,100,426 | 3/1992 | Nixon .................... 604/22 |
| 5,112,299 | 5/1992 | Pascaloff ............... 606/180 |
| 5,114,399 | 5/1992 | Kovalcheck ........... 604/22 |
| 5,152,744 | 10/1992 | Krause et al. ......... 606/180 |

FOREIGN PATENT DOCUMENTS

| | | |
|---|---|---|
| WO92/08416 | 5/1992 | PCT Int'l Appl. . |
| 1235321 | 6/1971 | United Kingdom . |
| 2222953A | 3/1990 | United Kingdom . |

SURGICAL DEVICE WITH SURGICAL ELEMENT REMOVABLY CONNECTED TO DRIVE ELEMENT

This is a continuation of application Ser. No. 07/600,531, filed Oct. 19, 1990, now abandoned.

BACKGROUND OF THE INVENTION

The invention relates to motor driven, rotatable surgical devices.

Surgical devices, e.g., for arthroscopy, typically include a one piece inner cylindrical tube and surgical tip or a surgical tip welded to an inner tube that rotates within an outer tube. The rotating surgical tip is exposed to tissue and bone through an opening in the distal end of the outer tube. In use, the proximal end of the device is inserted into a motor driven handpiece, which rotates the drive element and cutting element. The distal end of the outer tube is then inserted into a patient's body and advanced to a surgical site. The surgeon operates the device, i.e., rotates the cutting element in the outer tube to cut and remove tissue from the site, by activating the motor in the handpiece. Tissue and bone fragments cut by the tip, as well as irrigating fluid, are then suctioned through the interior of the inner tube and removed from the device. To prevent adhesive wear on and possible seizure of the rotating inner tube and surgical tip, it is important that both the tube and the tip have sufficient clearance within the outer tube, and that the tip be centered for rotation within the outer tube.

SUMMARY OF THE INVENTION

In one aspect, the invention features a device having a surgical element removably connected to a drive element so that drive torque is transmitted to the surgical element as the drive element rotates, while allowing the surgical element at least one degree of freedom of motion relative to the drive element; a retaining element maintains the drive and surgical elements in torque-transmitting relation during operation of the device.

Because of the loose connection of the surgical element and the drive element, during use the surgical element is able to align itself in the retaining element, offering a distinct advantage over devices in which a surgical element is rigidly attached to a drive element and may be undesireably off center. In addition, the invention allows the use of a standard drive element with any number of different surgical elements, and further allows the use of drive elements and surgical elements made of materials that cannot be welded or otherwise rigidly attached to one another.

Preferred embodiments have the following features. The drive and surgical elements are both tubular with a passage provided for suction removal of cut tissue; the two elements are removably connected to each other by circumferentially spaced engaging portions arranged to permit two degrees of freedom of motion between the connected elements, one along the axis of rotation of the surgical element and the other transverse to the axis. The retaining element is a tube surrounding the drive and surgical elements and extending beyond the distal end of the surgical element to provide an abutment limiting the axial degree of freedom and thereby holding the portions together for torque transmission. The retaining element and the drive element include threaded regions that serve as abutments to capture the drive element in the retaining element.

The tube fits closely about the drive and surgical elements to limit the degree of freedom transverse to the axis. The tube and the surgical element have cooperating cutting edges, with the tube having greater clearance around the drive element than around the surgical element, which can be achieved by providing a surgical element greater in diameter than the drive element, so that the cutting edges will fit closely while allowing an easy, non-binding fit around the drive element. Materials used in the device include stainless steel for the outer tube and surgical element, and stainless steel or plastic for the drive element. Other materials incompatible for welding or brazing may also be combined. Finally, the drive element may include a curved portion or a flexible portion, where the flexible portion may extend within and conform to a curved portion in the retaining element.

In another aspect, the invention features an elongated, rotatable, non-metallic drive element, and a surgical element having a portion removably connectable to the drive element for transmitting driving torque from the drive element to the surgical element, the surgical element being constructed of a metallic material sufficiently hard to remove tissue or bone during operation of the device.

Other advantages and features of the invention will be apparent from the following description of a preferred embodiment thereof and from the claims.

DESCRIPTION OF THE PREFERRED EMBODIMENT

Referring first briefly to the drawings.

STRUCTURE AND OPERATION

Figure 1:
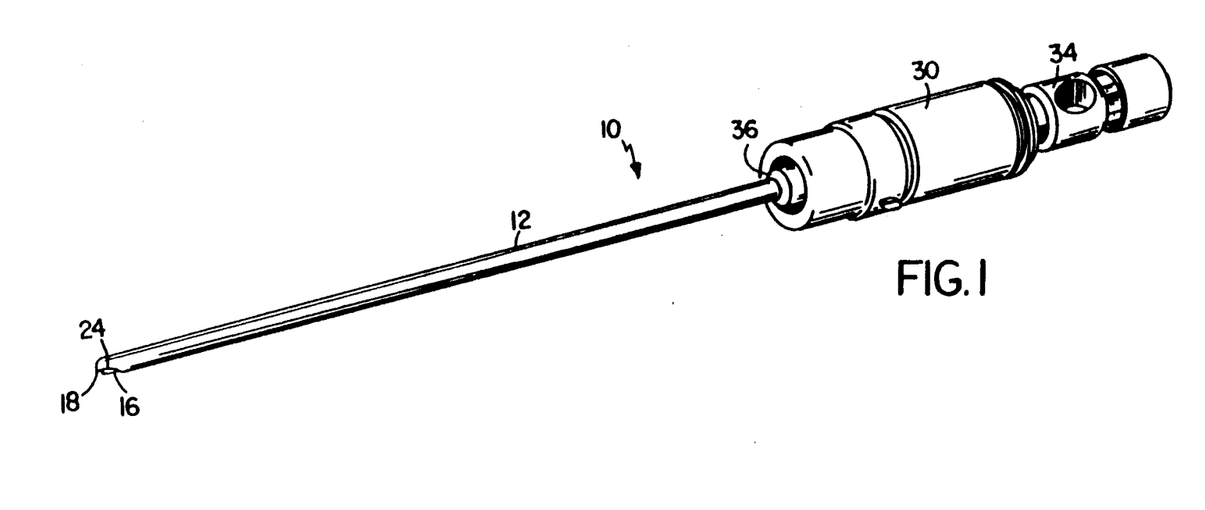
FIG. 1 is a perspective view of a surgical device embodying the invention.
Figure 2:
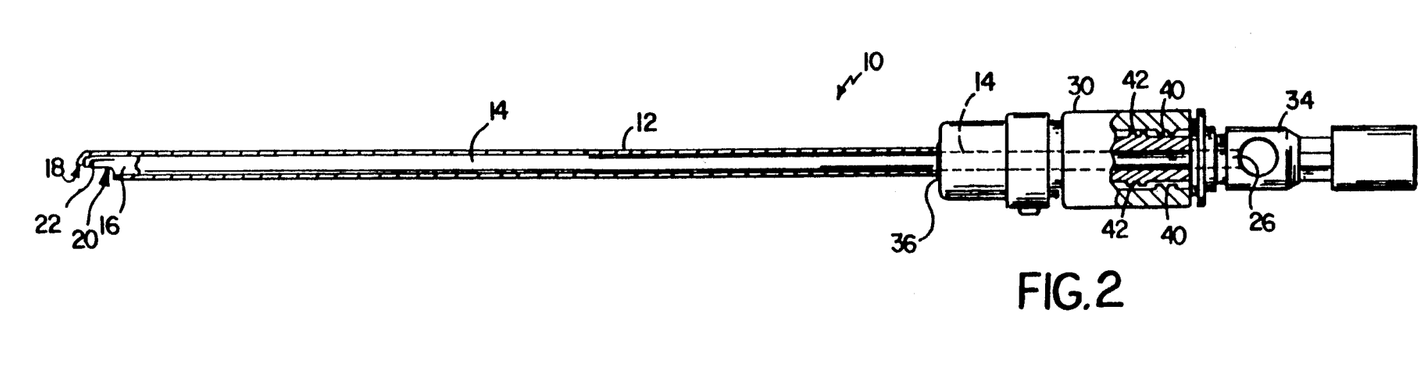
FIG. 2 is a side view, partly in cross section, of the device of FIG. 1.

Referring to FIGS. 1 and 2, a surgical device 10, e.g., for arthroscopic surgery on the knee, includes a rigid, stationary outer tube 12, within which rotates a rigid inner tube 14 (shown partly in dotted lines in FIG. 2), and a separate removable blade 16, also formed as a tube. The distal end of the outer tube 12 defines an opening 18 through which the blade 16 is exposed. Another opening 20 is defined in the blade 16. The sharpened edges 22 of the blade opening 20 cooperate with sharpened edges 24 of the outer tube opening 18 to shear tissue and bone during operation of the device. In addition, the blade opening 20 aligns with the outer tube opening 18 periodically as the inner tube 14 rotates, thereby admitting tissue and bone fragments into the interior of the blade 16 and connected inner tube 14. These fragments are then removed by suction through a central opening 26 in the inner tube 14 as described later in connection with FIG. 5.

Device 10 further includes a hub 30 and a rotatable drive shaft 34. The proximal end of the outer tube 12 is rigidly mounted to the hub 30 at a sealed joint 36, while the proximal end of the inner tube 14 is mounted and sealed to the drive shaft 34, which rotates within the hub 30. The hub 30 and drive shaft 34 include short threaded portions 40 and 42, respectively, which, after being engaged and screwed past each other, serve as abutments to prevent the drive shaft from sliding back out of the tube. A snap fit arrangement may be used instead of the threads to accomplish the same goal.

The device 10 may be disposable or reusable. For example, a disposable device designed for general purpose arthroscopic surgery will include an outer tube 12 and a blade 16 made from stainless steel sufficiently hard to remove tissue or bone during operation of the device. The hub 30 and drive shaft 34 may be made of plastic, and the inner tube 14 may also be made of plastic since, as explained below in connection with FIGS. 3 and 4, the blade 16 need not be welded to the inner tube. Reusable devices, however, will typically be made wholly of stainless steel.

Referring again to FIG. 1, the blade 16 is sized relative to the outer tube opening 18 so that it cannot fall out of the opening. The distal end of the blade 16 abuts the distal, partially capped, end of the outer tube 12 and is radially restrained within the outer tube. In addition, the motor housing within a handpiece 50 (shown in FIG. 5) presses axially on the drive shaft 34 to retain the connected inner tube 14 and blade 16 in close engagement with the outer tube 12.

Figure 3:
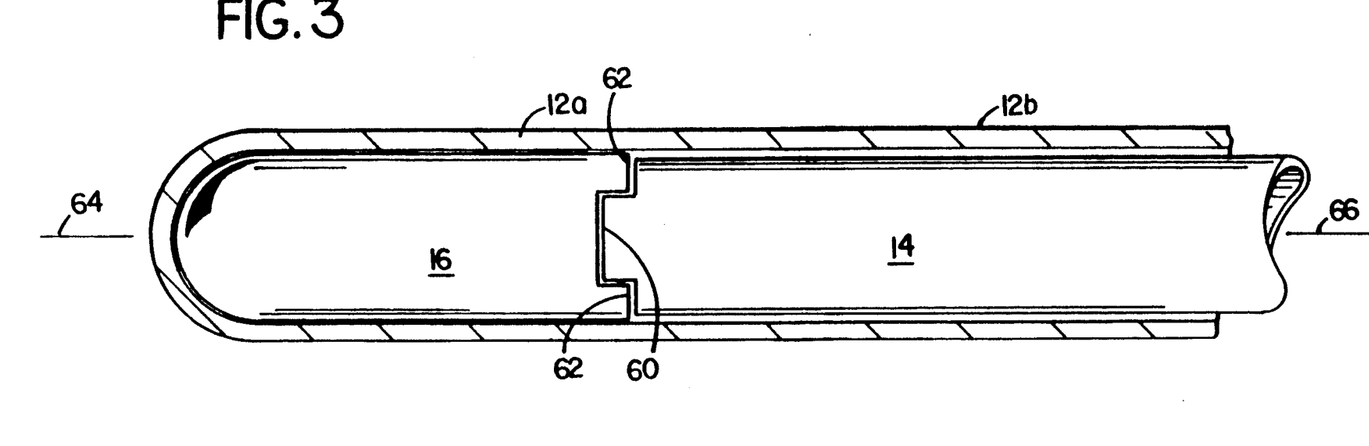
FIG. 3 is an enlarged view of the distal portion of the device of FIGS. 1 and 2, including the rigid outer tube, rotating inner tube, and blade tip.
Figure 4:
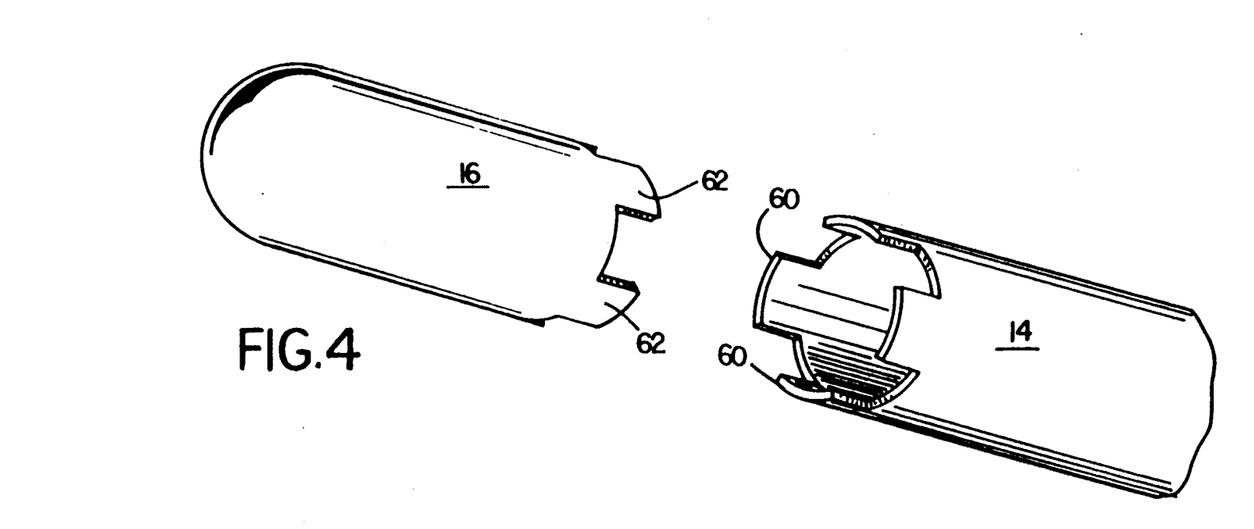
FIG. 4 is an exploded view of the blade tip and the distal end of the inner tube of FIG. 3, including the arrangement of portions by which the two pieces are connectable.

Referring to FIGS. 3 and 4, the clearance between the blade 16 and the outer tube 12, if desired, can be made less than that between the inner tube 14 and the outer tube so that the blade maintains a closer fit with the inner walls of the outer tube 12 and provides good cutting. This difference in clearance can be achieved by making the outer diameter of the blade 16 greater than that of the inner tube 14, or by stepping down the diameter of the outer tube 12 towards its distal end.

In an important aspect of the invention, the inner tube 14 is a thin-walled tube having a series of circumferentially spaced portions 60 at its distal end, which engage with a corresponding series of portions 62 on the proximal end of the blade 16. The engaging portions 60 and 62 provide a loose attachment of the inner tube 14 and the blade 16 and transmit torque from the rotating inner tube to the blade without requiring a weld or other rigid attachment between the pieces. The loose attachment provides two degrees of freedom of motion between the tube 14 and the blade 16, one generally along the axis of rotation 64 of the blade, and one transverse to the axis. The corners of the engaging portions 60 and 62 are rounded to facilitate engagement of the inner tube 14 and the blade 16. In alternative embodiments, the walls of the engaging portions 60 and 62 on the tube 14 and the blade 16 may be slightly sloped to further ease the engagement of the tube and the blade.

Allowing play between the inner tube 14 and the blade 16, and providing a blade which is separate from the inner tube, provides several advantages. During use of the device 10, for example, the blade 16 movably adjusts so that it rotates in alignment with the outer tube 12, because the blade is not rigidly attached to the inner tube 14 and is free to move relative to the inner tube. The separate inner tube and blade feature not only eliminates the expense and effort of welding, straightening, and centerless grinding the two pieces, but also avoids disadvantages of previously known welded blades and inner tubes, e.g., adhesive wear on the blade and seizure, encountered when the blade is undesireably joined off-center or at an angle to the inner tube. Furthermore, the present invention allows a standard inner tube to be joined with any number of different blades; and tubes and blades made of materials that are difficult or impossible to weld or braze together, e.g., ceramics, harder metals, and plastics, can, nonetheless, be used together effectively.

Figure 5:
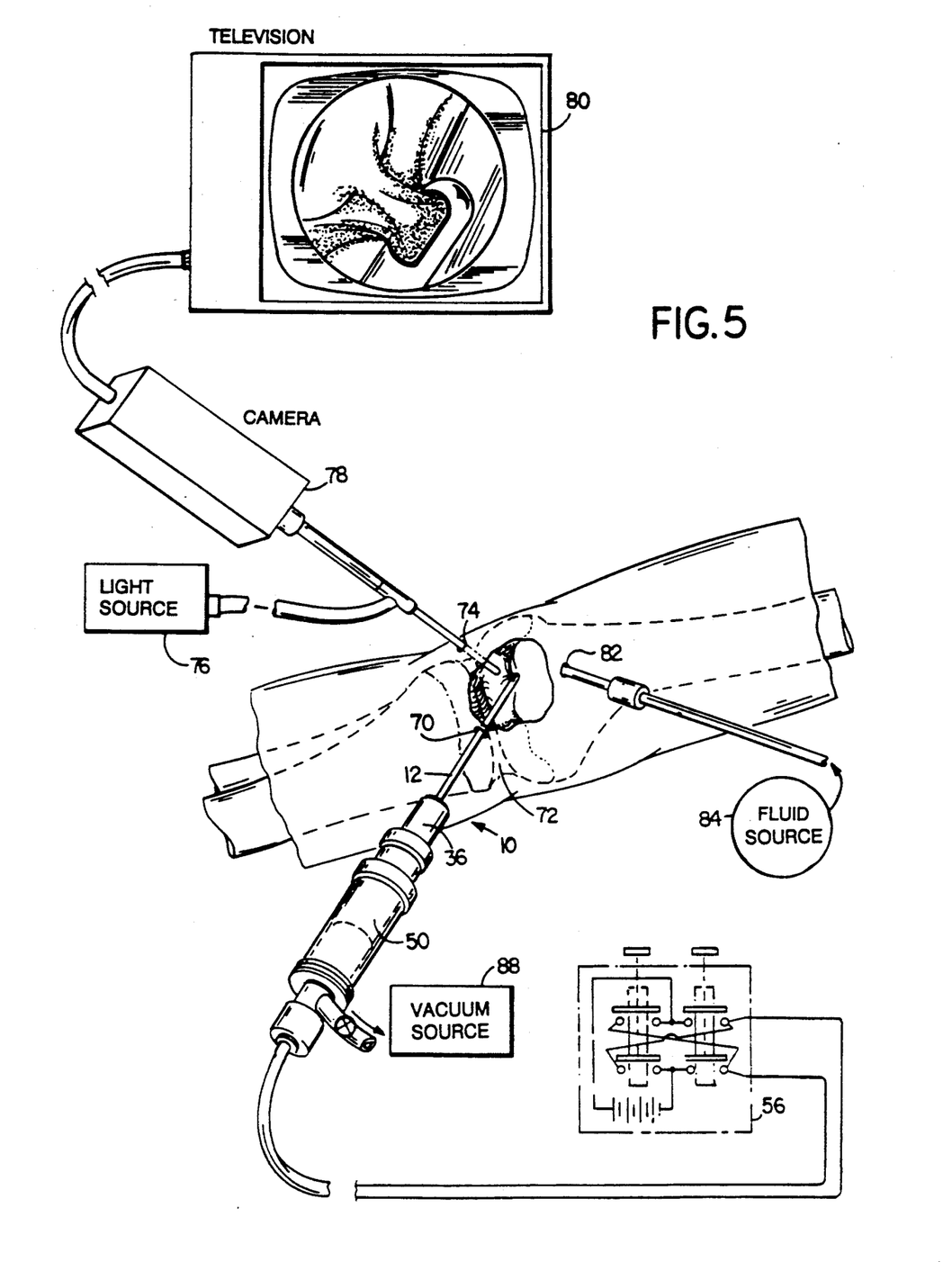
FIG. 5 illustrates the use of the device of FIG. 1 during surgery.
Figure 6:
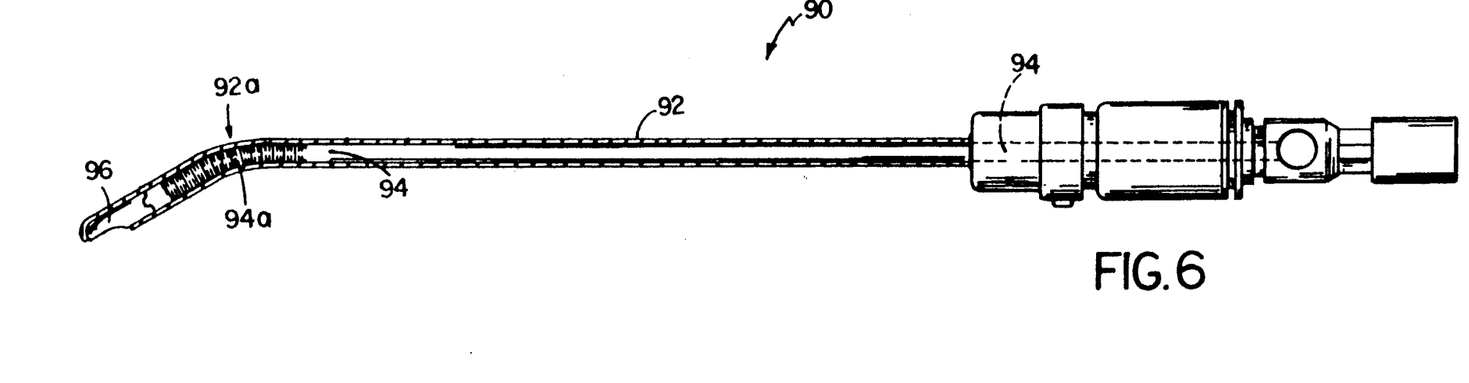
FIGS. 6 and 7 are side views, partly in cross section, of surgical devices having a curved distal portion, the first having an inner tube flexible at its distal portion, and the second having an inner tube flexible along all its length.

FIG. 6 shows a particularly advantageous use of the invention in a surgical device 90 having a curved distal portion, e.g., as described in pending patent application U.S. Ser. No. 07/477,223, assigned to the assignee of the present application and incorporated herein by reference. The device 90 has an outer tube 92, which is similar to the outer tube 12 described above in connection with FIGS. 1-5, except that the outer tube 92 is curved at a distal portion 92a. An inner drive tube 94, similar to the inner tube 14 described above in connection with FIGS. 1-5, fits within the outer tube 92 and is slotted to make it flexible at a distal portion 94a so that it conforms with the curved portion 92a of the outer tube. Removably connected to the distal end of the inner tube 94 is a blade tip 96, similar to blade tip 16 described above in connection with FIGS. 1-5. In alternative embodiments (not shown), the inner tube 94 can be made of a solid flexible plastic in the distal portion 94a, or can otherwise be made flexible, instead of being slotted.

Figure 7:
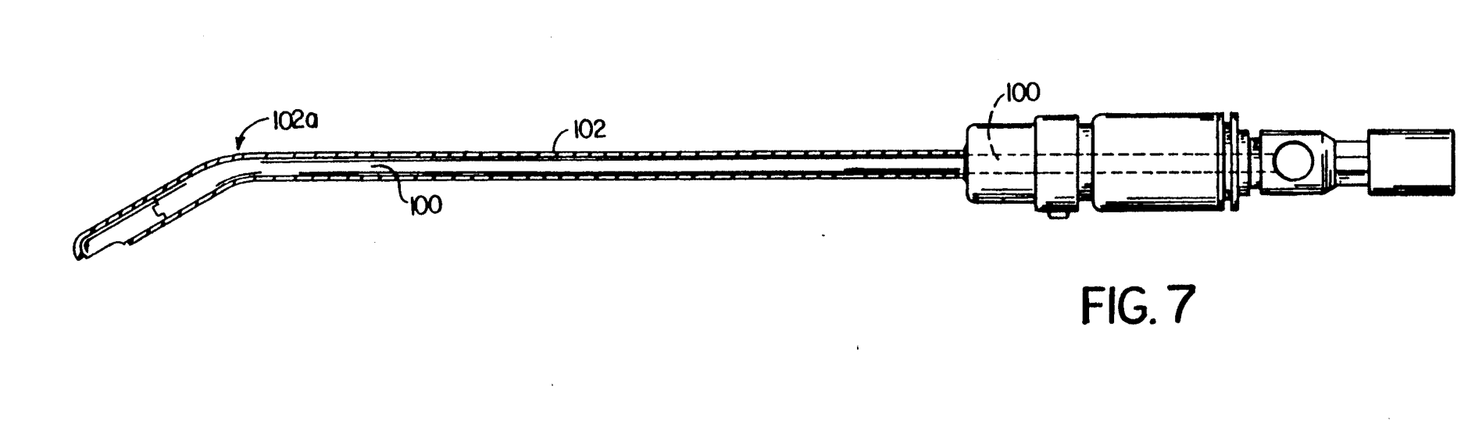

Referring to FIG. 7, an inner tube 100, similar to the inner tubes 14 and 94 described in connection with FIGS. 1-5 and FIG. 6, can be formed of a solid plastic material flexible along its length so that it conforms to a curved portion 102a in an outer tube 102. Alternative embodiments (not shown) include an inner tube slotted, or otherwise made flexible along its length, and further include surgical devices in which the outer tube itself is flexible, e.g., so that it can be directed through a catheter arrangement used during surgery on the back and hip regions of the body.

Referring to FIG. 5, in use, the proximal end of the drive shaft 34 is fitted into a handpiece 50, which includes a motor (not shown) for rotating the drive shaft 34, inner tube 14, and blade tip 16 (shown in FIGS. 1-2). An example of such a handpiece is described in U.S. Pat. No. 4,705,038, which is incorporated herein by reference. For arthroscopic surgery of the knee, the device 10 is inserted onto the distal end of a handpiece 50 and then introduced through a puncture wound 70 into a knee joint 72, below the patella. Light is projected into the joint 72 through a second puncture wound 74 by a fiber optic light source 76. A visual image of the surgical site is then returned through a separate optical path to a television camera 78 and displayed on a television screen 80 for the surgeon to view. (Alternatively, the surgeon can view the image through an eyepiece, or the image can be recorded.)

To rotate the inner tube 14 and blade 16, the surgeon activates a motor (not shown) in the handpiece 50, which is connected to a power supply 56. During surgery, the joint 72 is inflated with fluid introduced through a third puncture wound 82 by a fluid source 84. The fluid distends the joint 72, flushes blood out of the joint to give the surgeon a clear view of the area, and carries away any cut tissue. Viewing the image of the site on the television screen 80, the surgeon progressively cuts away the synovial tissue by moving the device 10 from side to side and axially. Tissue fragments cut by the device 10 and fluids are simultaneously withdrawn from the site through the opening 26 in the inner tube 14 in response to suction applied by a vacuum source 88.

It will be appreciated that the device described above can have additional embodiments. For example, many types of arthroscopic cutting elements can be used as an alternative to the blade shown and described. These tools include shavers, cutters, and abraders, as described in U.S. Pat. Nos. 4,203,444, 4,274,414, 4,522,206, 4,662,371, 4,834,729, and 4,842,578, all of which are incorporated by reference and assigned to the assignee of the present invention.

Other embodiments are within the following claims.

I claim:

1. A rotatable surgical device comprising:
    a stationary element having an opening disposed in a distal region thereof for admitting tissue;
    a rotatable drive element disposed within said stationary element, said drive element having a proximal end configured to be coupled to a source for rotating the drive element with respect to said stationary element about an axis of rotation, and a distal end having an axially extending surface; and
    a surgical element disposed within said stationary element for cutting tissue that is admitted through said opening, said surgical element having a portion removable connectable to said distal end of said drive element for transmitting driving torque from said drive element to said surgical element while allowing said surgical element at least one degree of freedom of motion relative to said drive element, said portion having an axially extending surface that is engaged by the axially extending surface of said drive element during rotation thereof;
    said distal region of said stationary element being at least partially closed distally of said opening to provide an abutment against which said drive element urges said surgical element during rotation to maintain said drive element and surgical element in torque-transmitting relation, said distal region being configured to maintain an amount by which said axially extending surfaces engage each other substantially constant throughout the rotation of the drive element.

2. The device of claim 1 wherein said at least one degree of freedom of motion includes a degree of freedom of motion that is transverse to the axis of rotation, said stationary element limiting said degree of freedom of motion transverse to the axis of rotation, while permitting said surgical element to align itself relative to said stationary element during rotation.

3. The device of claim 1 wherein said stationary element comprises a generally cylindrical tube, said drive element is an elongated member rotatable within said cylindrical tube, and said surgical element is removably connectable to a distal end of said elongated member.

4. The device of claim 3 wherein said stationary element is further constructed to retain at least a portion of said drive element within said cylindrical tube.

5. The device of claim 4 wherein said cylindrical tube and said proximal end of said drive element each include an abutment for retaining said portion of said drive element within said cylindrical tube.

6. The device of claim 5 wherein said stationary element and said proximal end of said drive element are threaded to provide said abutment.

7. The device of claim 1 or 3 wherein said drive and surgical elements each have circumferentially spaced portions which include said axially extending surfaces and which are arranged so that said axially extending surfaces engage each other to transmit torque from said drive element to said surgical element, while permitting said removable connection between said drive and surgical elements.

8. The device of claim 1 further comprising a passage disposed between said surgical element and said proximal end of said drive element to permit surgically removed body material to be withdrawn from said device through said passage by suction.

9. The device of claim 8 wherein said passage extends through the interior of said drive element and said surgical element.

10. The device of claim 1 wherein said opening in said stationary element, and said surgical element, have edges arranged to interact to provide surgical cutting as said drive element rotates.

11. The device of claim 1 wherein said stationary element comprises a generally cylindrical tube within which said drive element and said surgical element are disposed, and a clearance between said cylindrical tube and said surgical element is less than a clearance between said cylindrical tube and said drive element.

12. The device of claim 11 wherein said surgical element has an outside diameter larger than that of said drive element, so that the clearance between said surgical element and said cylindrical tube is less than the clearance between said drive element and said cylindrical tube.

13. The device of claim 1 wherein said drive and surgical elements are of different materials.

14. The device of claim 13 wherein said different materials are incompatible for welding or brazing.

15. The device of claim 14 wherein said drive element comprises a nonmetallic material and said surgical element comprises a metal.

16. The device of claim 15 wherein said drive element comprises plastic.

17. The device of claim 1 wherein said surgical element is replaceable.

18. A rotatable surgical device comprising:
    a stationary element having an opening disposed in a distal region thereof for admitting tissue;
    a rotatable drive element disposed within said stationary element, said drive element having a proximal end configured to be coupled to a source for rotating the drive element with respect to said stationary element about an axis of rotation, and a distal end having an axially extending surface;
    a handpiece for rotating said drive element; and
    a surgical element disposed within said stationary element for cutting tissue that is admitted through said opening, said surgical element having a proximal portion removably connectable to said distal end of said drive element for transmitting driving torque from said drive element to said surgical element while allowing said surgical element at least one degree of freedom of motion relative to said drive element, said proximal portion having an axially extending surface that is engaged by the axially extending surface of said drive element during rotation thereof;

said distal region of said stationary element being at least partially closed distally of said opening to provide an abutment against which said drive element urges said surgical element during rotation to maintain said drive element and surgical element in torque-transmitting relation, said distal region being configured to maintain an amount by which said axially extending surfaces engage each other substantially constant throughout the rotation of the drive element.

19. The device of claim 18 wherein said handpiece contains a motor for rotating said drive element.

20. The device of claim 18 wherein said handpiece includes a port connectable to a suction device.

21. The device of claim 20 further comprising a passage disposed between said surgical element and said suction port to permit surgically removed body material to be withdrawn from said device through said passage by suction through said passage and said suction port.

22. The device of claim 21 wherein said passage extends through the interior of said drive element and said surgical element.

23. The device of claim 8 or 21 wherein said body material comprises tissue.

24. The device of claim 8 or 21 wherein said body material comprises bone.

25. The device of claim 18 wherein said surgical element has two degrees of freedom of motion relative to said drive element, a second said degree of freedom of motion being transverse to the axis of rotation, said stationary element limiting said second degree of freedom of motion transverse to the axis of rotation while permitting said surgical element to align itself relative to said stationary element during rotation.

26. The device of claim 1 or 18 wherein said stationary element includes a curved portion, a portion of said drive element being flexible and disposed within said curved portion.

27. The device of claim 1 or 18 wherein said drive element is flexible along at least a portion of a length thereof.

28. The device of claim 27 wherein said drive element is flexible along a major portion of said length.

29. The device of claim 1 or 18 wherein said stationary element is configured to maintain the axis of rotation of said drive element substantially parallel to an axis of rotation of said surgical element at least in a region in which said distal end of said drive element engages said portion of said surgical element.

30. The device of claim 29 wherein said stationary element is configured to maintain said axes of rotation substantially coincident.

31. The device of claim 1 or 18 wherein said stationary element is substantially straight at least in a region in which said distal end of said drive element engages said portion of said surgical element.

32. The device of claim 1 or 18 wherein said stationary element is configured to maintains aid axially extending surfaces of said drive element in substantially full engagement with said axially extending surfaces of said surgical element during said rotation.

33. A rotatable surgical device comprising
a stationary element having an opening disposed in a distal region thereof for admitting tissue;
a drive element disposed within said stationary element, said drive element being rotatable with respect to said stationary element about an axis of rotation and having a plurality of spaced tabs each of which includes a pair of axially extending edges that terminate at a surface disposed transversely to said edges; and
a surgical element disposed within said stationary element for cutting tissue that is admitted through said opening, said surgical element having a portion removable connectable to said drive element for transmitting driving torque from said drive element to said surgical element while allowing said surgical element at least one degree of freedom of motion relative to said drive element, said portion having a plurality of spaced tabs configured to be disposed between said spaced tabs of said drive element, each of said spaced tabs of said portion including a pair of axially extending edges that terminate at a surface disposed transversely to said axially extending edges of said portion and that engage said axially extending edges of said spaced tabs of said drive element;
said distal region of said stationary element being at least partially closed distally of said opening to provide an abutment against which said drive element urges said surgical element during rotation to maintain said drive element and said surgical element in torque-transmitting relation, said distal region being configured to maintain one of said axially extending edges of each of said spaced tabs of said drive element in engagement with one of said axially extending edges of each of said spaced tabs of said surgical element throughout the rotation of the drive element.

34. The device of claim 33 wherein said said axially extending edges of said tabs of said drive element and said surgical element are disposed substantially parallel to said axis of said device.

* * * * *

UNITED STATES PATENT AND TRADEMARK OFFICE
CERTIFICATE OF CORRECTION

PATENT NO.  : 5,320,635

DATED       : June 14, 1994

INVENTOR(S) : Graham Smith

It is certified that error appears in the above-identified patent and that said Letters Patent is hereby corrected as shown below:

On the title page:
In the References Cited section, please add the following reference:

"Angleblade Surgical Instrument, Bowen & Company, Inc., Rockville, Maryland".

Col. 8, claim 34, line 51, "said device" should be --rotation--.

Signed and Sealed this

Fifteenth Day of November, 1994

Attest:

BRUCE LEHMAN

Attesting Officer

Commissioner of Patents and Trademarks